United States Patent [19]

Cihonski

[11] 4,225,738

[45] Sep. 30, 1980

[54] PRODUCTION OF HIGH PURITY BUTADIENE

[75] Inventor: John L. Cihonski, Odessa, Tex.

[73] Assignee: El Paso Products Company, Odessa, Tex.

[21] Appl. No.: 32,290

[22] Filed: Apr. 23, 1979

[51] Int. Cl.³ .......................... C07C 5/00; C07C 5/333
[52] U.S. Cl. .................................. 585/506; 585/366; 585/367; 585/832
[58] Field of Search ................ 585/506, 366, 367, 832

[56] References Cited

U.S. PATENT DOCUMENTS

| | | | |
|---|---|---|---|
| 2,355,392 | 8/1944 | Oberfell | 585/832 |
| 2,423,179 | 7/1947 | Doumani et al. | 585/366 |
| 2,433,465 | 12/1947 | Leum et al. | 585/832 |
| 4,117,025 | 9/1978 | Liebert et al. | 585/832 |

*Primary Examiner*—Jacqueline V. Howard

[57] ABSTRACT

This invention provides a three-step process for converting n-butene into high purity 1,3-butadiene, via a vinylcyclohexene intermediate.

In the first step of the process, n-butene and molecular oxygen are contacted with a Group VIII metal oxide catalyst. If nitrobenzene is employed as the oxidizing agent in place of molecular oxygen then aniline is produced as a secondary product of the process.

12 Claims, No Drawings

PRODUCTION OF HIGH PURITY BUTADIENE

BACKGROUND OF THE INVENTION

Light petroleum byproduct streams from refinery operations constitute a potentially valuable source of commercially important olefinic feedstocks.

A C₄ fraction of gases from vapor phase cracking of petroleum oil usually contains less than about 15-20 percent of butadiene in admixture with other C₄ hydrocarbons. Likewise, the pyrolysis of butane under conventional conditions converts to butadiene in low yield.

In commercial processes which utilize butadiene it is essential that the butadiene feedstock is provided in concentrated form. For example, in the production of synthetic rubber by copolymerization of butadiene with a monomer such as acrylonitrile, the butadiene feedstock must have a purity of at least about 90 percent or higher.

Various methods have been developed which have as a main object the provision of conjugated diolefinic hydrocarbons such as butadiene in highly concentrated form suitable for commercial polymerization reactions.

U.S. Pat. No. 2,355,392 describes a process for the separation of a low-boiling acyclic diolefin from a mixture of hydrocarbons all of which have boiling points within a narrow range. The process involves (1) subjecting the hydrocarbon mixture to elevated temperature and pressure to promote dimerization of the diolefin, (2) separating the dimer compound from the other components of the resultant product mixture, and (3) subjecting the dimer to depolymerization conditions in the presence of steam to effect conversion of the dimer to the corresponding monomeric product. Optionally, a polymerization catalyst such as oxygen or hydrogen peroxide is employed in the first step, and a depolymerization catalyst such as bauxite is employed in the second step of the process.

U.S. Pat. No. 2,423,179 describes a process for concentrating conjugated dienes containing fewer than seven carbon atoms from mixtures containing them in small proportions which involves (1) subjecting such a mixture to elevated temperatures between about 600°-1100° F. and pressures between about 50-5000 psi in the presence of an oxygen-bearing hydrocarbon derivative having dimerization accelerating properties, thereby forming diene dimers, (2) separating the dimerized products from the residual materials, and (3) depolymerizing the dimerized product to yield the diene monomer in concentrated form by subjecting the dimer to temperatures between about 1200°-1600° F. under partial pressure below atmospheric.

U.S. Pat. No. 2,433,465 describes a process for effecting the separation of a hydrocarbon mixture containing isobutylene, n-butene and butadiene which involves (1) subjecting the mixture to a non-selective thermal polymerization treatment at a temperature between 800°-1000° F. and a pressure of 500-2000 psi, (2) contacting the resulting polymers with a depolymerization catalyst at a temperature between 400°-800° F. to reproduce the isobutylene in monomeric form, (3) separating the reproduced monomeric isobutylene from the unconverted polymers, (4) contacting the unconverted polymers with a depolymerization catalyst at a temperature between 800°-900° F. to reproduce the n-butene in monomeric form, and (5) separating the reproduced monomeric n-butene from the unconverted polymers still remaining.

There remains a need for practical and economical methods for the separation of the components of light hydrocarbon mixtures which are difficult to separate by conventional fractionation means. There is further need for an improved process for deriving concentrated diolefinic hydrocarbon fractions from petroleum refinery light hydrocarbon byproduct streams.

Accordingly, it is an object of this invention to provide a process for the improved separation and utilization of the components of light hydrocarbon mixtures which are difficult to separate.

It is another object of this invention to provide a process for deriving a concentrated diolefinic fraction from a petroleum refinery light hydrocarbon byproduct stream.

It is a further object of this invention to provide a process for converting a C₄ hydrocarbon mixture into high purity butadiene with minimal production of acetylenes.

Other objects and advantages of the present invention shall become apparent from the accompanying description and examples.

DESCRIPTION OF THE INVENTION

One or more objects of the present invention are accomplished by the provision of a process for the production of high purity 1,3-butadiene which comprises the steps of (1) contacting n-butane with a Group VIII metal oxide or hydroxide catalyst in the presence of molecular oxygen at a temperature between about 130° C. and 500° C. and a pressure between about 1 and 200 psi to convert the n-butene feed to an intermediate product mixture containing vinylcyclohexene, wherein said vinylcyclohexene is produced with a conversion efficiency of at least 65 weight percent; (2) removing C₄-hydrocarbons from the intermediate product mixture; and (3) subjecting the product mixture to a temperature between about 500° C. and 1000° C. and a pressure between about 1 and 200 psi for a period of time between about 0.01 and 10 seconds to yield a normally gaseous product consisting substantially of 1,3-butadiene.

The reaction can be conducted as a batch or continuous procedure. The first step of the process described above can be performed either in the liquid or vapor phase. As a liquid phase reaction, the first step of the process is preferably conducted at a temperature between about 130° C. and 300° C. for a reaction period between 1 and 10 hours.

The third step of the process must be conducted in the vapor phase if optimal conversion efficiency of vinylcyclohexene to the desired high purity butadiene is to be achieved.

$$CH_2=CH-CH_2-CH_3$$

and/or $$CH_3-CH=CH-CH_3 \xrightarrow{-H_2}$$

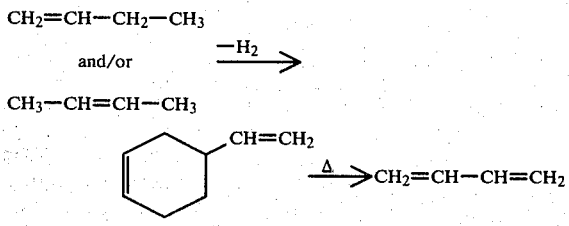

The n-butene feedstock can be either 1-butene or 2-butene, or a mixture thereof. This invention also contemplates the use of feedstocks which are mixtures of n-butene with other light paraffinic hydrocarbons such as butane, isobutane, isobutylene, butadiene, n-octenes and the like. Butane, butadiene and n-octenes are susceptible to conversion to vinylcyclohexene under the conditions of the present invention process. It is an important advantage of the present invention process that the light hydrocarbon mixture employed as a feedstock need not contain any butadiene, since n-butene is the preferred hydrocarbon raw material for conversion to the desired high purity butadiene product.

In the case where the first step of the present invention process is conducted in the vapor phase, suitable reactors for the conversion of n-butene include either fixed bed or fluid bed reactors which contain at least one Group VIII metal oxide or hydroxide catalyst component. The gas fed to a reactor comprises n-butene and molecular oxygen to which nitrogen, carbon dioxide, steam or the like may optionally be added as an inert diluent. Unreacted n-butene feed can be recycled in the process if desired.

The first step reaction is conducted at temperatures between about 130° C. and 500° C., and preferably at a temperature between about 150° C. and 300° C. The residence time (i.e., catalyst contact time) of the feed stream in the first step reaction is between about 0.5 and 20 seconds, and preferably between about 1 and 15 seconds. Residence time refers to the contact time adjusted to 25° C. and atmospheric pressure. The contact time is calculated by dividing the volume of the catalyst bed (including voids) by the volume per unit time flow rate of the feed stream at NTP.

The intermediate product mixture which is the effluent from the first step vapor phase reaction consists of both normally gaseous and normally liquid components. Thus, in the second step of the process, the required removal of $C_4$-hydrocarbons from the normally liquid components of the intermediate product mixture is readily accomplished by conventional fractionation procedures. The normally liquid fraction of the intermediate product mixture consists of vinylcyclohexene as the major component, and in addition contains smaller proportions of ethylbenzene and styrene.

It is not necessary to use pure oxygen as the source of oxygen in the first step of the process. Air is a suitable source of oxygen and is desirable for reasons of economy. Alternatively, the oxidizing agent can be ozone (under conditions which prevent direct interaction of ozone and olefin) or a compound which can generate oxygen under reaction conditions (e.g., peroxides and hydroperoxides), or it can be a compound which contains an active-oxygen functional group (e.g., nitro derivatives). Aliphatic and aromatic nitro compounds which have a boiling point below about 250° C. are particularly useful as an oxidizing agent in place of molecular oxygen in the first step of the invention process. Thus, in another embodiment this invention provides a means for the ancillary production of aniline which comprises contacting n-butenes with a Group VIII metal oxide or hydroxide catalyst in the presence of nitrobenzene at a temperature between about 200° C. and 500° C. and a pressure between about 1 and 200 psi to yield an intermediate product mixture which contains aniline in addition to vinylcyclohexene, ethylbenzene and styrene.

The pressure utilized in the first step vapor phase reaction zone can be subatmospheric, atmospheric or superatmospheric. A preferred pressure for the first step vapor phase process is one which is in the range between about 1 and 200 psi.

In any of the embodiments of the present invention process, the quantity of molecular oxygen (or its equivalent) introduced into the first step reaction system theoretically should be at least sufficient to satisfy the stoichiometry of the oxidative conversions. The molar ratio of oxygen to 1-butene feed can vary broadly over the range between about 0.1:1 and 10:1. A molar ratio of oxygen to 1-butene of about 1:1 has been found to be convenient and effective.

The catalyst employed in the first step of the invention process is selected from one or more Group VIII metals which are in an oxidized state (e.g., an oxide or a hydroxide). The preferred Group VIII metals are nickel, palladium and platinum, with palladium being the most preferred Group VIII metal species.

The catalyst can be prepared by adding an alkali (e.g., sodium or potassium hydroxide) to a solution of one or more water soluble Group VIII metal compounds, such as the chlorides, nitrates and sulfates of nickel, palladium and platinum. The precipitate which forms is recovered, washed with water, and dried.

It has been found that the activity of the catalyst is enhanced if the prepared catalyst is calcined in air at a temperature between about 250° C. and 500° C. for a period of about 3–24 hours.

The Group VIII metal oxide or hydroxide composition described can be used as the catalyst per se, but it is preferred that the said composition is combined with a suitable internal diluent or carrier substrate.

The carrier substrate should be relatively refractory to the conditions utilized in the invention process. Suitable carrier substrate materials include (1) silica or silica gel, silicon carbide, clays, and silicates including those synthetically prepared and naturally occurring, which may or may not be acid treated such as attapulgus clay, china clay, diatomaceous earth, Fuller's earth, kaolin, asbestos and kieselguhr; (2) ceramics, porcelain, crushed firebrick and bauxite; (3) refractory inorganic oxides such as alumina, titanium dioxide, zirconium dioxide chromium oxide, beryllium oxide, vanadium oxide, cesium oxide, hafnium oxide, zinc oxide, magnesia, boria, thoria, silica-alumina, silica-magnesia, chromia-alumina, alumina-boria, silica-zirconia, molybdenum oxide, bismuth oxide, uranium oxide and tungsten oxide; (4) crystalline zeolitic alumino-silicates such as naturally occurring or synthetically prepared mordenite and/or faujasite, either in the hydrogen form or in a form which has been treated with multivalent cations; and (5) spinels such as $MgAl_2O_4$, $FeAl_2O_4$, $ZnAl_2O_4$, $MnAl_2O_4$, $CaAl_2O_4$, and other like compounds having the formula $MO.Al_2O_3$ where M is a metal having a valence of 2.

As mentioned previously, the intermediate product mixture from the first step of the process is subjected to a conventional fractionation procedure to remove any $C_4$-hydrocarbons (and any molecular oxygen or other low molecular weight gaseous materials) from the normally liquid components consisting essentially of vinylcyclohexene, ethylbenzene and styrene. Preferably the first step reaction conditions are controlled to yield vinylcyclohexene with at least 65 weight percent conversion efficiency from n-butene. The presence of butane, butadiene and/or n-octene in the feedstock proportionally increases the yield of vinylcyclohexene, ethylbenzene and styrene in the intermediate product mixture.

For the purposes of the third step procedure of the invention process, it is not necessary to separate the vinylcyclohexene from the other normally liquid components of the intermediate reaction product mixture recovered from the second step. In the third step of the invention process, the vinylcyclohexene (alone or with ethylbenzene and styrene) is subjected to a temperature between about 500° C. and 1000° C., preferably a temperature between about 550° C. and 750° C., and a pressure between about 1 and 200 psi for a reaction period between about 0.01 and 5 seconds, preferably for a reaction period between about 0.1 and 5 seconds, to yield 1,3-butadiene in a purity of at least 90 weight percent, and more preferably in a purity of at least 95 weight percent.

It is possible to convert vinylcyclohexene into 1,3-butadiene in essentially quantitative yield if optimal processing conditions are provided. For example, if vinylcyclohexene is vaporized and blended with an inert diluent such as steam (in a molar ratio between about 1:1 and 1:20 of vinylcyclohexene to steam), and heated at a temperature between about 550° C. and 750° C. and a pressure between about 1 and 200 psi (preferably with the partial pressure of the cyclohexene being less than about 15 psi) for a reaction time between about 0.1 and 5 seconds and at a single pass vinylcyclohexene conversion rate of 5–25 percent, 1,3-butadiene product of at least 98 weight percent purity can be obtained. It is advantageous to quench the 1,3-butadiene product stream as it exits from the third step heating zone. The presence of an inert diluent, plus a rapid quench, function to minimize loss of product due to thermal polymerization of the 1,3-butadiene molecules.

It can be advantageous to employ a cracking catalyst in the third step heating zone, to facilitate control of the temperature, pressure and flow rate parameters, or to permit an increase in the conversion efficiency of the vinylcyclohexene to 1,3-butadiene under less severe temperature conditions.

Suitable cracking catalysts include Fuller's earth, bentonite, acid-activated bentonite or clay, silicon carbide, bauxite, activated alumina, oxides and sulfides of Group VI metals, alkaline earth metal oxides, rare earth oxides, naturally occurring and synthetic crystalline zeolitic aluminosilicates, and the like, which can include other catalytic elements such as copper, silver, iron, palladium and platinum, rare earth metals, and the like.

Any of the catalysts employed in the first and third steps of the invention process can be in the shape of granules, pellets, extrudate, powders, tablets, or other such convenient physical form.

The following examples are further illustrative of the present invention. The reactants and other specific ingredients are presented as being typical, and various modifications can be derived in view of the foregoing disclosure within the scope of the invention.

EXAMPLE I

To a solution of 20 grams of palladium chloride in 100 milliliters of 0.5 N hydrochloric acid and 400 milliliters of water, is added 100 grams of asbestos and a quantity of 0.5 N sodium hydroxide solution equivalent to the total chloride concentration in the resultant admixture. After a 30 minute refluxing period, the precipitate is separated by filtration, washed with water, and dried at 200° C. for 24 hours.

The recovered catalyst is calcined in air at a temperature of 300° C. for 24 hours, and then crushed and sieved to yield 20–30 mesh catalyst particles. About 5 $cm^3$ of the catalyst composition are blended with about 10 $cm^3$ mesh crushed fused quartz and charged into a 7 mm I.D. glass tube reactor.

A gaseous feed is prepared by admixing 1-butene and air in proportions which provide about a 1:1 molar ratio of 1-butene to molecular oxygen.

The feed mixture is passed through the tube reactor at a temperature of about 250° C. under autogenous pressure at a rate providing a catalyst contact time of about 10 seconds.

The effluent stream is quenched to a temperature below about 100° C. to separate the unreacted 1-butene and other volatile components from the normally liquid components.

The conversion of 1-butene per single pass is 18 percent and the conversion efficiency (i.e., selectivity), based on the total weight of liquid product, is 67 weight percent vinylcyclohexene, 27 weight percent ethylbenzene, and 6 weight percent styrene.

The mixture of normally liquid products is fractionated by distillation to separate the vinylcyclohexene from the other components.

The vinylcyclohexene is vaporized and blended with steam in a 1:10 molar ratio of vinylcyclohexene to steam, and passed through an empty tube reactor at a temperature of 675° C. and a pressure of about 1 atmosphere. The residence time of the feedstream in the heating zone is about 2 seconds, and the single pass conversion of cyclohexene averages in the range of 10–20 percent. The effluent from the reactor is rapidly quenched to below 100° C.

The product gas which is recovered consists of 1,3-butadiene of 98+ percent purity, as determined by GC analysis.

EXAMPLE II

Following the same procedure and employing the same first step catalyst as described in Example I, n-butene is converted to high purity 1,3-butadiene using nitrobenzene as the oxidizing component instead of molecular oxygen in the first step dehydrocyclodimerization reaction.

The n-butene consists of a 1:1 molar ratio of 1-butene/2-butene. The nitrobenzene is employed in an approximately equimolar quantity relative to the n-butene.

The feed mixture is passed through the tube reactor at a temperature of about 280° C. and a pressure of about 1 atmosphere, and at a flow rate providing a catalyst contact time of about 5 seconds.

After the effluent stream from the tube reactor is quenched, the normally liquid components are recovered as a liquid mixture consisting of vinylcyclohexene, ethylbenzene, styrene, nitrobenzene and aniline.

The liquid mixture is fractionally distilled, and the vinylcyclohexene product is converted to 98+ purity 1,4-butadiene employing approximately the same pyrolysis conditions as described in Example I.

The unreacted nitrobenzene is recycled in the process, and the aniline is separated out as a product of the process.

What is claimed is:

1. A process for the production of high purity 1,3-butadiene which comprises the steps of (1) contacting n-butene with a Group VIII metal oxide or hydroxide catalyst in the presence of molecular oxygen at a temperature between about 130° C. and 500° C. and a pressure between about 1 and 200 psi to convert the n- butene feed to an intermediate product mixture containing vinylcyclohexene, wherein said vinylcyclohexene is produced with a conversion efficiency of at least 65 weight percent; (2) removing $C_4$-hydrocarbons from the intermediate product mixture; and (3) subjecting the product mixture to a temperature between about 500° C. and 1000° C. and a pressure between about 1 and 200 psi for a period of time between about 0.01 and 10 seconds to yield a normally gaseous product consisting substantially of 1,3-butadiene.

2. A process in accordance with claim 1 wherein the Group VIII metal catalyst in step (1) is selected from palladium, platinum and nickel oxides and hydroxides.

3. A process in accordance with claim 1 wherein the Group VIII metal catalyst in step (1) is supported on a carrier substrate.

4. A process in accordance with claim 1 wherein the 1-butene and molecular oxygen reactants in step (1) are employed in about an equimolar ratio.

5. A process in accordance with claim 1 wherein the normally liquid components of the intermediate product mixture produced in step (1) consist substantially of vinylcyclohexene, ethylbenzene and styrene.

6. A process in accordance with claim 1 wherein the heat treatment of the intermediate product mixture in step (3) is conducted in the presence of a cracking catalyst.

7. A process in accordance with claim 1 wherein the partial pressure of the vinylcyclohexene in the step (3) heating zone is less than about 15 psi.

8. A process in accordance with claim 1 wherein the intermediate product mixture in vapor phase is diluted with an inert gas medium before it is introduced into the step (3) heating zone.

9. A process in accordance with claim 8 wherein the inert gas medium is steam, carbon dioxide or nitrogen.

10. A process in accordance with claim 1 wherein the product of the process is 1,3-butadiene of at least 95 weight percent purity.

11. A process in accordance with claim 1 wherein a compound selected from aliphatic and aromatic nitro compounds having a boiling point below about 250° C. is employed as the oxidizing agent in place of molecular oxygen in the first step of the process.

12. A process in accordance with claim 11 wherein the oxidizing agent is nitrobenzene, and aniline is a product of the process.

* * * * *